United States Patent [19]

Yamashita

[11] Patent Number: 4,623,737

[45] Date of Patent: Nov. 18, 1986

[54] SYNTHESIS OF PRECURSORS OF ANTI-ATHEROSCLEROTIC FUROCHROMONES

[75] Inventor: Ayako Yamashita, Kalamazoo, Mich.

[73] Assignee: The Upjohn Company, Kalamazoo, Mich.

[21] Appl. No.: 679,523

[22] Filed: Dec. 7, 1984

[51] Int. Cl.$^4$ ............................................. C07D 307/86
[52] U.S. Cl. ................................... 549/471; 549/214; 549/370; 549/448; 549/470
[58] Field of Search ............... 549/214, 370, 448, 470, 549/471; 260/438.5 R

[56] References Cited

U.S. PATENT DOCUMENTS

| | | | |
|---|---|---|---|
| 2,680,119 | 6/1954 | Robertson et al. | 260/345.2 |
| 4,284,569 | 8/1981 | Gammill | 260/345.2 |
| 4,320,065 | 3/1982 | Dötz | 260/438.5 R |
| 4,434,296 | 2/1984 | Gammill | 549/471 |
| 4,459,420 | 7/1984 | Gammill | 549/471 |

OTHER PUBLICATIONS

Yamashita et al., Tet. Letters, vol. 26, pp. 2969–2972 (1985).
Yamashita, J. Am. Chem. Soc., vol. 107, pp. 5823–5824, (1985).
Dötz et al., Chem. Ber. 111, pp. 2517–2526 (1978).
Yamashita et al., Tet. Letters, vol. 23, No. 37, pp. 3765–3768 (1982).
Cram et al., Organic Chem.–McGraw-Hill (1959) pp. 172–174.
A. Mustafa, Benzofurans, John Wiley & Sons, Contents, pp. 1–13 (1974).
A. Mustafa, Furopyrans and Furopyrones, Chapter 3, pp. 102–159 (1967).
L. R. Row, et al., Indian J. Chem., 5:105–106 (1967).
J. R. Clarke, et al., J. Chem. Soc., pp. 302–307 (1949).
R. A. Baxter, et al., J. Chem. Soc., S30–S33 (1949).
A. Schonberg, et al., J. Am. Chem. Soc., 73:2960–2961 (1951).
V. V. S. Murti, et al., Proc. of the Indian Acad. of Sci., 30A:107–113 (1949).
T. A. Geissman, et al., J. Am. Chem. Soc., 73:1280–1284 (1951).
R. B. Gammill, et al., J. Org. Chem., 48:3863–3865 (1983).
R. B. Gammill, et al., J. Med. Chem., 26:1672–1674 (1983).
E. Spath, et al., Chem. Ber., 71:106–113 (1938).
O. Dann, et al., Chem. Ber., 93:2829–2833 (1960).
O. Dann, et al., Ann. Chem., 605:146–157 (1957).
V. V. S. Murti, et al., J. Sci. Ind. Res. (India), 8B, 23:107–113 (1949).
R. Aneja, et al., Chem. Ber., 93:297–303 (1960).
R. Aneja, et al., J. Sci. Ind. Res., (India), 17B:382–383 (1958).
T. S. Gardner, et al., J. Org. Chem., 15:841–849 (1950).
C. Musante, Gazz. Chim. Ital., 88:910–929 (1958).

*Primary Examiner*—Henry R. Jiles
*Assistant Examiner*—Bernard I. Dentz
*Attorney, Agent, or Firm*—Martha A. Cox

[57] ABSTRACT

The present invention provides novel compositions of matter and processes for their preparation. More particularly, the present invention consists of novel chemical intermediates and associated processes for the preparation of khellin and analogues thereof, which have demonstrated antiatherosclerotic activity.

4 Claims, No Drawings

SYNTHESIS OF PRECURSORS OF ANTI-ATHEROSCLEROTIC FUROCHROMONES

BACKGROUND OF THE INVENTION

The present invention provides novel compositions of matter and processes for their preparation. Particularly, the present invention relates to novel chemical intermediates and associated processes for the preparation of both known and novel precursors of khellin and other furochromone analogues, which have demonstrated lipid-altering and antiatherosclerotic activity. See U.S. Pat. No. 4,284,569.

Khellin and related compounds are known to exert a wide variety of pharmacological effects. Recently, khellin has been reported to exhibit useful antiatherosclerotic activities. Moreover, numerous analogues of khellin likewise are known to exert useful antiatherosclerotic effects. For example, 7-methylthiomethyl-4,9-dimethoxyfurochromone is described in U.S. Pat. No. 4,284,569 as such a useful antiatherosclerotic substance.

INFORMATION DISCLOSURE

Methods of the total synthesis of khellin are known, as are certain chemical intermediates useful in its synthesis. For example, the total synthesis of furochromones from benzofurans has been accomplished by utilizing a substituted benzene ring from which to synthesize the fused benzofuran ring system. See A. Mustafa, "Benzofurans" (1974) and A. Mustafa, "Furopyrans and Furopyrones, Chapter 3: Furochromones" (1967). Pyrogallol has been employed as a starting material for the synthesis of khellin and antiatherosclerotic analogues thereof. See U.S. Pat. No. 4,459,420; L. R. Rowe et al., *Indian J. Chem.* 5: 105 (1967); J. R. Clarke et al., *J. Chem. Soc.* 302 (1949); R. A. Baxter et al., *J. Chem. Soc.* S30 (1949); A. Schonberg et al., *J. Am. Chem. Soc.*, 73: 2960 (1951); V. V. S. Murti et al., *Proc of the Indian Acad. of Sci.* 30A: 107 (1949); and T. A. Geissman et al., *J. Am. Chem. Soc.* 73: 1280 (1951). Also, 3-furoic acid has been transformed to benzofuran intermediates useful in the synthesis of khellin and khellin analogues. See U.S. Pat. No. 4,434,296; Ser. No. 668,765, filed Nov. 11, 1984; R. B. Gammill and B. R. Hyde, *J. Org. Chem.* 48: 3863 (1983). See also R. B. Gammill, C. E. Day, and P. E. Schurr, *J. Med. Chem.* 26: 1672 (1983); U.S. Pat. No. 4,284,569.

Also descriptive of the synthesis of khellin are E. Spath et al., *Chem. Ber.* 71: 106 (1938), O. Dann et al., *Chem. Ber.* 93: 2829 (1960), O. Dann et al., *Ann. Chem.* 605: 146 (1957), and V. V. S. Murti et al., *J. Sci. Ind. Res.* (India) 8B: 112 (1949). See also U.S. Pat. No. 2,680,119 describing the synthesis of khellin and related compounds.

Other references describing the synthesis of intermediates useful in the preparation of khellin or analogues include: R. Aneja et al., *Chem. Ber.* 93: 297 (1960), R. Aneja et al., *J. Sci. Ind. Res.* (India) 17B: 382 (1958), T. S. Gardner et al., *J. Org. Chem.* 15: 841 (1950), and L. R. Row et al., *Indian J. Chem.* 5: 105 (1967).

Accordingly, the references cited above describe the preparation of 1-(6-hydroxy-4,7-dimethoxy-5-benzofuranyl)-ethanone. Also known is the related compound 6-hydroxy-4,7-dimethoxy-5-benzofurancarboxylic acid, methyl ester, described by C. Musante *Gazz. Chim. Ital.* 88: 910 (1958).

SUMMARY OF THE INVENTION

The present invention particularly provides:

(1) A process for preparing a compound of the formula II
wherein $R_1$ is $-C(O)-R_2$;
wherein $R_2$ is $(C_1-C_5)$n-alkyl;
wherein $R_4$ is
  (a) $-SiR_{12}R_{13}R_{14}$,
  (b) benzyl, or
  (c) benzyl substituted by 1 to 3 $(C_1-C_4)$alkyl or 1 to 3 $(C_1-C_4)$methoxy groups;
wherein $R_7$ is
  (a) hydrogen,
  (b) $-C(O)-R_6$, or
  (c) $-C(OR_{20})(OR_{21})R_6$;
wherein $R_6$ is
  (a) $(C_1-C_8)$alkyl,
  (b) $(C_2-C_8)$alkoxymethyl,
  (c) trifluoromethyl,
  (d) phenoxymethyl,
  (e) phenylthiomethyl, or
  (f) $-CH_2-S(O)_n-R_{22}$;
wherein n is 0, 1, or 2;
wherein $R_{12}$, $R_{13}$, and $R_{14}$ are the same or different and are:
  (a) $(C_1-C_4)$alkyl, or
  (b) phenyl;
wherein $R_{20}$ and $R_{21}$ are the same or different and are
  (a) $(C_1-C_4)$alkyl, or
  (b) $R_{20}$ and $R_{21}$ taken together form a cyclic group of from 5 to 6 atoms; and
wherein $R_{22}$ is $(C_1-C_5)$alkyl;
which comprises reacting a chromium compound of the formula III with an acetylenic compound of the formula IV in the presence of a solvent, an acid anhydride of the formula XI and triethylamine to yield the formula II compound;

(2) A process for preparing a compound of the formula IX
wherein $R_{31}$ is $(C_1-C_5)$alkyl;
which comprises treating a compound of the formula X with a Lewis acid to yield the formula IX compound;

(3) A process for preparing a compound of the formula VII
wherein $R_{11}$ is methyl or ethyl; and
consisting essentially of reacting a chromium compound of the formula III with an acetylenic compound of the formula VIII in the presence of a solvent to yield the formula VII compound;

(4) A process for preparing a compound of the formula VII(a) which comprises reacting a chromium compound of the formula III with an acetylenic compound of the formula VIII(a) to yield the formula VII(a) compound; and (5) A compound of the formula I
wherein $R_3$ is
  (a) hydrogen,
  (b) $(C_1-C_5)$alkyl, or
  (c) $-C(O)-R_2$;
wherein $R_2$ is $(C_1-C_5)$n-alkyl;
wherein $R_7$ is
  (a) hydrogen,
  (b) $-C(O)-R_6$, or
  (c) $-C(OR_{20})(OR_{21})R_6$;
wherein M is divalent and is
  (a) $=O$, or
  (b) $-H$, $-OR_4$;

wherein $R_4$ is
  (a) —$SiR_{12}R_{13}R_{14}$,
  (b) benzyl, or
  (c) benzyl substituted by 1 to 3 ($C_1$–$C_4$)alkyl or 1 to 3 ($C_1$–$C_4$)methoxy groups;
wherein $R_6$ is
  (a) ($C_1$–$C_8$)alkyl,
  (b) ($C_2$–$C_8$)alkoxymethyl,
  (c) trifluoromethyl,
  (d) phenoxymethyl,
  (e) phenylthiomethyl, or
  (f) —$CH_2$—$S(O)_n$—$R_{22}$;
wherein n is 0, 1, or 2;
wherein $R_{12}$, $R_{13}$, and $R_{14}$ are the same or different and are:
  (a) ($C_1$–$C_4$)alkyl, or
  (b) phenyl;
wherein $R_{20}$ and $R_{21}$ are the same or different and are
  (a) ($C_1$–$C_4$)alkyl, or
  (b) $R_{20}$ and $R_{21}$ taken together form a cyclic group of from 5 to 6 atoms; and
wherein $R_{22}$ is ($C_1$–$C_5$)alkyl.

The carbon atom content of various hydrocarbon-containing moieties is indicated by a prefix designating the minimum and maximum number of carbon atoms in the moiety, i.e., the prefix ($C_i$–$C_j$) indicates a moiety of the integer "i" to the integer "j" carbon atoms, inclusive. Thus, for example, ($C_1$–$C_3$)alkyl refers to alkyl of one to three carbon atoms, inclusive, or methyl, ethyl, propyl, and isopropyl.

Examples of alkyl of one to nine carbon atoms, inclusive, are methyl, ethyl, propyl, butyl, pentyl, hexyl, heptyl, octyl, and nonyl, and isomeric forms thereof. n-Alkyl shall refer to only the straight chain isomer of these compounds. Examples of n-alkyl of one to five carbon atoms are methyl, ethyl, n-propyl, n-butyl and n-pentyl.

The compounds of the present invention will be named herein using the Chemical Abstracts numbering system (see "Naming and Indexing of Chemical Substances for Chemical Abstracts during the Ninth Collective Period (1972-1976)," a reprint of section IV from the Volume 76 Index Guide).

The process of the present invention is more completely understood by reference to the charts below. Charts A, B, and C herein describe three methods by which khellin is prepared from a furyl chromium carbene complex. In these charts, "Bu(t)" represents the tert-butyl group and the other variables are as defined above.

With respect to Chart A, the chromium carbene complex of formula A-1, the acetylene of formula A-2, and an acid anhydride of formula A-3 are used as the starting materials. Pentacarbonyl[2-furyl(methoxy)carbene]-chromium of formula A-1 may be prepared by standard methodology described in E. O. Fischer et al., J. Organometal. Chem., 16 (1969) P29-P32; K. H. Dötz et al., Chem. Ber. 111: 2517 (1978); A. Yamashita et al., Tet. Lett. 23: 3765 (1982); Ser. No. 561,601, filed Dec. 14, 1983; Ser. No. 668,111, filed Nov. 5, 1984. The acetylene of formula A-2 may be prepared from the commercially available ethoxyacetylene by standard methodology. Commercially available ethoxyacetylene is treated with n-butyl lithium in tetrahydrofuran (THF) at −78° C., followed by treatment with the proper aldehyde (e.g., 3-ethylenedioxybutyraldehyde, acetaldehyde) at −78° C. under argon. The resulting solution is poured into water, extracted with ether, giving the ethoxy-bearing acetylene alcohol. The alcohol may be protected with the appropriate protecting group (e.g., t-butyldimethylsilyl group) by using standard methodology (e.g., t-butyldimethylsilylchloride, imidazole in dimethylformamide). See G. Stock and M. Tomasz, J. Am. Chem. Soc. 86: 471 (1964). The acid anhydride of formula A-3 may be prepared by standard methodology which is known in the art.

In Chart A, the reaction of the formula A-1 chromium carbene complex and the formula A-2 acetylene in tetrahydrofuran in the presence of an acid anhydride of the formula A-3 and triethylamine under an argon atmosphere requires heating for several days, yielding the benzofuran derivative of formula A-4. See Ser. No. 561,601, filed Dec. 14, 1983; Ser. No. 668,111 filed Nov. 5, 1984. The parallel reaction of the chromium carbene complex and the acetylene in the presence of an acid anhydride, without triethylamine, requires almost one week for completion.

The $R_1$ group of the formula A-4 compound is converted to the $R_{31}$ group of the formula A-5 compound by treatment with a base (e.g., potassium carbonate, sodium hydride) and the corresponding halide (e.g., methyl iodide) in an appropriate solvent (e.g., tetrahydrofuran) under an inert gas atmosphere. This reaction requires several days for completion and produces the formula A-5 compound.

The t-butyldimethylsilyl group is cleaved from the formula A-5 compound by standard methodology. The reaction of the formula A-5 compound with tetra-n-butyl ammonium fluoride trihydrate in dimethylformamide or tetrahydrofuran under argon for several hours gives the alcohol of formula A-6.

The formula A-6 compound is oxidized with known oxidants (e.g., pyridinium dichromate) in dry methylene chloride to yield the formula A-7 ketone.

Treatment of the formula A-7 compound with an appropriate oxidant (e.g., cerric ammonium nitrate) in a suitable solvent system (e.g., a mixture of water and acetonitrile) using the Rappaport method, J. Org. Chem., 46: 2745 (1981), converts the benzene ring to the transitory quinone of formula A-8. Treatment of the formula A-8 intermediate with acid (e.g., 1N hydrochloric acid in tetrahydrofuran) yields the formula A-9 khellin trione.

The formula A-9 trione is reduced by heating on a steam bath with an excess of sodium bisulfite and a catalytic amount of concentrated hydrochloric acid and is dimethylated by treating with excess potassium carbonate and methyl iodide in acetone. Thick layer chromatography isolates isokhellin of formula A-10 and khellin of formula A-11. See O. Dann and H. G. Zeller, Chem. Ber. 93: 2829 (1960). See also V. V. S. Meverti and T. R. Sishodin, Proc. Indian Acad. Sci. 30A: 107 (1949); J. R. Clarke and Robertson, J. Chem. Soc. 302 (1949).

Chart B depicts an alternative method by which khellin may be prepared. Treatment of the formula B-1 compound with a Lewis acid (e.g., boron trifluoride etherate in dry methylene chloride or aluminum chloride in nitrobenzene) under argon selectively cleaves the aryl ethyl group at the six position, in the presence of two other aryl alkyl groups, and produces the hydroxybenzofuran derivative of formula B-2.

Claisen condensation of the formula B-2 compound with ethyl acetate in the presence of sodium hydride, followed by acid treatment (e.g., an aqueous solution of 1N hydrochloric acid in methanol) affords the formula B-3 khellin and analogues thereof. See E. Spath and W. Gruber, *Chem. Ber.* 71: 106 (1938); T. A. Geissman and T. G. Halsall, *J. Am. Chem. Soc.* 73: 1280 (1951); R. B. Gammill and B. R. Hyde, *J. Org. Chem.* 48: 3865 (1983). See U.S. Pat. No. 4,284,569.

With respect to Chart C, the chromium carbene complex of formula C-1 and the acetylene of formula C-2 are used as the starting materials. The reaction of the formula C-1 carbene complex and the formula C-2 acetylene (e.g., ethylpropiolate) in a suitable solvent (e.g., tetrahydrofuran, ether) under argon at elevated temperatures affords the benzofuran ester of formula C-3. The formula C-3 ester is converted to the formula C-4 methyl ketone by standard methodology. Alternatively, reaction of the formula C-1 chromium carbene complex and acetylacetylene of formula C2(a) in a suitable solvent (e.g., tetrahydrofuran, ethyl ether) under an argon atmosphere at an elevated temperature produces the formula C-4 compound directly. The formula C-4 compound is then converted to khellin of formula C-5. See Ser. No. 668,765, filed Nov. 6, 1984.

DESCRIPTION OF THE PREFERRED EMBODIMENTS

The preparation of the compounds described in the instant specification is more readily understood by the following examples. In these examples, all $^1$H-NMR spectra are recorded on either Varian FT-80A or Wilmad WCV-XLFT-100 instruments. Chemical shifts are expressed in parts per million ($\delta$) downfield from internal tetramethylsilane. All IR-spectra are taken on Perkin-Elmer Model 297 or Digilab Model FTS 140 instruments. All melting points and boiling points are uncorrected. The term "under argon" means that the reaction vessel is alternately evacuated to 0.01 torr and filled with argon at least three times. Dry solvents are distilled before use from an appropriate drying agent. Tetrahydrofuran (THF) is distilled under argon from sodium metal-benzophenone ketyl immediately before use. Triethylamine, diisopropylamine and dimethylformamide (DMF) are distilled under argon from calcium hydride and stored under argon. Acetic anhydride, methyl iodide, 1-ethoxy-5-ethylenedioxy-3(t)butyldimethylsilyloxy-1-hexyne, and 1-ethoxy-3(t)butyldimethylsilyloxy-1-butyne are distilled under argon and stored under argon. Dry methylene chloride is distilled from phosphorous pentoxide under argon. All other reactants and solvents are ACS reagent grade unless described otherwise. "Ether" refers to anhydrous diethyl ether which is supplied by Mallinckrodt and Baker. Preparative thin-layer chromatography (TLC) is conducted on 20×20 cm glass plates with 2000 micron thickness of Silica Gel G (manufactured by E. Merck and Co., Germany). Silica gel column for flash chromatography utilizes E. Merck silica gel 60 (230–400 mesh, American Society for Testing Materials).

EXAMPLE 1

4-Acetoxy-5-[1'-(t)-butyldimethyl-silyloxy-3'-ethylenedioxybutyl]-6-ethoxy-7-methoxy-benzofuran (Formula A-4: $R_1$ is acetyl; $R_7$ is —C(O$R_{20}$)(O$R_{21}$)$R_6$; $R_{20}$ and $R_{21}$ taken together form a cyclic group of 5 atoms; $R_6$ is methyl).

A. Reaction of pentacarbonyl[$\alpha$-furyl(methoxy)carbene]chromium (Formula A-1) with 1-ethoxy-5-ethylenedioxy-3-(t)-butyldimethylsilyloxy-1-hexyne (Formula A-2) in the presence of acetic anhydride (Formula A-3) and triethylamine.

To a mixture of the Formula A-1 carbene complex (3.0 g, 9.9 mmole) and the Formula A-2 acetylene (3.0 g, 9.9 mmole) in 280 ml of THF (freshly distilled), prepared under an argon atmosphere, are added Formula A-3 acetic anhydride (0.94 ml, 9.9 mmole) and triethylamine (1.4 ml, 9.9 mmole) via syringe. The resulting dark red solution is heated at 65° C. (bath temperature) under argon for 3 days at which time the TLC analysis shows that most of the carbene complex is consumed and the color of the solution is dark brown. The solution is cooled and concentrated by rotary evaporation. The dark tarry residue is dissolved in 50 ml of methylene chloride and 200 ml of n-hexane, and 100 ml of ether are added. The greenish-brown precipitate is removed by filtering through the Celite and the filtrate is concentrated to dryness. The residue is loaded on a silica gel column (200 g of silica gel used) for a flash chromatography. Elution by 10–20% ether in n-hexane isolates 1.363 g (27.9%) of the title product as a brown oil.

Physical characteristics are as follows:
Mass spectra (m/e): 494, 393, 351, 293, 115 and 87.
IR (cm$^{-1}$): 1769, 1478, 1264, and 1053.
Analysis Calcd. for: $C_{25}H_{38}O_8Si$: C, 60.70; H, 7.74. Found: C, 60.45; H, 7.71.
$^1$H-NMR ($\delta$, CDCl$_3$): 7.51, 6.52, 5.65–5.40, 4.09, 3.88, 4.25–3.95, 2.32, 1.55–1.20, 0.92 and 0.14.

B. Reaction of pentacarbonyl[$\alpha$-furyl(methoxy)carbene]-chromium (Formula A-1) with 1-ethoxy-5-ethylenedioxy-3-(t)-butyldimethyl-silyloxy-1-hexyne (Formula A-2) in the presence of acetic anhydride (Formula A-3).

To a solution of the Formula A-1 carbene complex (2.5 g, 8.3 mmole) and the Formula A-2 acetylene (2.5 g, 8.3 mmole) in 250 ml of THF, prepared under an argon atmosphere, is added Formula A-3 acetic anhydride (1.2 ml, 12.5 mmole). The resulting deep red solution is heated at 65° C. (bath temperature) under argon. After heating at this temperature for 5 days, TLC analysis shows the carbene complex is not completely consumed. The solution is cooled and concentrated by rotary evaporation to give a dark brown tar, which is loaded on a silica gel column (200 g silica gel used) for a flash chromatography. Elution by 5% ether in n-hexane gives 545 mg (15%) of 5-[1'-(t)-butyldimethylsilyloxy-3'-ethylenedioxybutyl]-6-ethoxy-4-hydroxy-7-methoxybenzofuran as a brown oil. Elution by 10–20% ether in n-hexane gives 546 mg (13.3%) of the title product as a brown oil.

Physical characteristics are as follows:
5-[1'-(t)-Butyldimethylsilyloxy-3'-ethylenedioxybutyl]-6-ethoxy-4-hydroxy-7-methoxy-benzofuran:
Mass spectra (m/e): 452, 351, 293, 259, 234, and 87.
Mass Calcd. for: $C_{23}H_{36}O_7Si$: 452.2230. Found: 452.2234.
IR(cm$^{-1}$): 3328, 1659, 1477, and 1054.
$^1$H-NMR ($\delta$, CDCl$_3$): 8.46, 7.46, 6.81, 5.60–5.40, 4.23, 4.00, 3.93, 2.55–1.75, 1.46, 1.44, 0.89, 0.20, and −0.07.
Anal. Calcd. for $C_{23}H_{36}O_7Si$: C, 61.03; H, 8.02. Found: C, 61.07; H, 8.15.
4-Acetoxy-5-[1-(t)-butyldimethyl-silyloxy-3'-ethylenedioxybutyl]-6-ethoxy-7-methoxy-benzofuran:
Physical properties are the same as those of Example 1(A).

EXAMPLE 2

5-[1'-(t)-Butyldimethylsilyloxy-3'-ethylenedioxybutyl]-4,7-dimethoxy-6-ethoxybenzofuran (Formula A-5: $R_{31}$ is methyl; $R_7$ is —$C(OR_{20})(OR_{21})R_6$; $R_{20}$ and $R_{21}$ taken together form a cyclic group of 5 atoms; $R_6$ is methyl). Preparation of 5-[1'-(t)-butyldimethylsilyloxy-3'-ethylenedioxybutyl]-4,7-dimethoxy-6-ethoxybenzofuran.

To a cooled (ice bath) suspension of sodium hydride (50% oil dispersion) (155 mg, 3.2 mmole) and sodium hydroxide (solid, 40 mg, 1.04 mmole) in 30 ml of THF is added a solution of the benzofuran acetate of Formula A-4 (500 mg, 1.04 mmole) in 20 ml of THF under an argon atmosphere. The resulting solution is stirred at 0° C. (ice bath) for 1 hour and an excess (2 ml) of methyl iodide is added. The ice bath is removed and the brown solution is stirred at 23° C. for 3 days at which time TLC analysis shows no starting material is left. The reaction solution is poured into 10 ml of a mixture of ice and water, and the aqueous layer is extracted three times with 100 ml of ether. The extracts are combined, washed three times with 100 ml of brine, dried over anhydrous sodium sulfate, filtered and concentrated by rotary evaporation. The products are isolated by using 2000 micron silica gel plate developed twice by ether:-hexane (1:5 mixture), giving 6 mg (1.3%) of 4-(t)-butyl-dimethylsilyloxy-5-(3'-ethylendioxy-1'-butenyl)-6-ethoxy-7-methoxy-benzofuran as a yellow oil, 330 mg (68.1%) of the title product as a yellow oil, and 80 mg (23.1%) of 5-3'-ethylenedioxy-1'-butenyl)-4,7-dimethoxy-6-ethoxybenzofuran as a yellow oil.

Physical properties of the products are as follows:
4-(t)-Butyldimethylsilyloxy-5-(3'-ethylenedioxy-1'-butenyl)-6-ethoxy-7-methoxybenzofuran:
 Mass spectra (m/e): 434, 419, and 87.
 Mass calcd. for $C_{23}H_{34}O_6Si$: 434.2124. Found: 434.2117.
 IR(cm$^{-1}$): 1463, 1348, 1211, 1131, and 1056.
 $^1$H-NMR ($\delta$, CDCl$_3$): 7.46, 6.69, 6.70, 4.06, 3.97, 4.25–3.90, 1.53, 1.39, 1.07, and 0.15.
5-[1'-(t)-Butyldimethylsilyloxy-3'-ethylenedioxybutyl]-4,7-dimethoxy-6-ethoxy-benzofuran:
 Mass spectra (m/e): 466.
 Mass Calcd. for $C_{24}H_{38}O_7Si$: 466.2387. Found: 466.2395.
 IR(cm$^{-1}$): 1614, 1478, 1377, 1343, 1246, 1132, and 1063.
 $^1$H-NMR ($\delta$, CDCl$_3$): 7.50, 6.81, 5.60–5.30, 4.04, 3.97, 3.86, 4.25–3.90, 2.70–1.80, 1.32, 1.44, 0.83 and 0.14.
 Anal. calcd. for $C_{24}H_{38}O_7Si$: C, 61.77; H, 8.21. Found: C, 62.12; H, 8.28.
5-(3'-Ethylenedioxy-1'-butenyl)-4,7-dimethoxy-6-ethoxybenzofuran:
 Mass spectra (m/e): 334, 319, 113, 111, and 87.
 Mass Calcd. for $C_{18}H_{22}O_6$: 334.1416. Found: 334.1225.
 IR(cm$^{-1}$): 1476, 1385, 1267, and 1043.
 $^1$H-NMR ($\delta$, CDCl$_3$): 7.52, 6.82, 6.71, 4.07, 3.99, 3.90, 1.39, and 1.40.

EXAMPLE 3

4,7-Dimethoxy-5-(3'-ethylenedioxy-1'-hydroxybutyl)-6-ethoxybenzofuran (Formula A-6: $R_{31}$ is methyl; $R_7$ is —$C(OR_{20})(OR_{21})R_6$; $R_{20}$ and $R_{21}$ taken together form a cyclic group of 5 atoms; $R_6$ is methyl). Preparation of 4,7-dimethoxy-5-(3'-ethylenedioxy-1'-hydroxybutyl)-6-ethoxybenzofuran.

A solution of the silyloxy benzofuran of Formula A-5 (1.39 g, 3.2 mmole) and tetra-n-butylammonium fluoride trihydrate (3.0 g, 9.6 mmole) in 50 ml of dimethylformamide, prepared under an argon atmosphere, is heated at 50°–55° C. (bath temperature) under argon for 20 hours. The resulting dark solution is cooled and diluted with 500 ml of ether. The ether extract is washed five times with 200 ml of brine, dried over anhydrous sodium sulfate, filtered and concentrated by rotary evaporation. The residue is loaded on 2000 micron silica gel plates (developed twice by ether:n-hexane (1:1 mix)), giving 985 mg (87.2%) of the title product as a yellow oil.

Physical characteristics are as follows:
 Mass spectra (m/e): 352, 251, and 87.
 Mass Calcd. for $C_{18}H_{24}O_7$: 352.1522. Found: 352.1505.
 IR(cm$^{-1}$): 3519, 1480, 1384, 1343, 1131, and 1062.
 $^1$H-NMR ($\delta$, CDCl$_3$): 7.51, 6.82, 5.57–5.30, 4.40–4.00, 4.05, 4.01, 3.63, 2.75–1.80, 1.48, and 1.44.
 Analysis Calcd. for $C_{18}H_{24}O_7$: C, 61.35; H, 6.86. Found: C, 61.14; H, 6.90.

EXAMPLE 4

4,7-Dimethoxy-5-[3'-ethylenedioxy-1'-oxo]-butyl-6-ethoxybenzofuran (Formula A-7: $R_{31}$ is methyl; $R_5$ is —$C(OR_{20})$—$(OR_{21})R_6$; $R_{20}$ and $R_{21}$ taken together form a cyclic group of 5 atoms; $R_6$ is methyl). Preparation of 4,7-dimethoxy-5-[3'-ethylenedioxy-1'-oxo]butyl-6-ethoxybenzofuran.

To a mixture of the corresponding benzofuran alcohol of Formula A-6 (686 mg, 1.95 mmole) and pyridinium dichromate (2.2 g, 5.85 mmole), prepared under argon, is introduced 90 ml of dry methylene chloride at room temperature. The resulting dark brown solution is stirred at 23° C. for 2 days under argon. The solution is diluted with 100 ml of methylene chloride and filtered through the Celite cake. The filtrate is concentrated by rotary evaporation and the residue is loaded on 2000 micron silica gel plates, which are developed by n-hexane:ether (5:3 mixture) three times. The title product is isolated in 34.9% (238 mg) yield.

The physical properties of the ketone are as follows:
 Mass spectra (m/e): 350, 249, 221, 220, and 87.
 Mass Calcd. for $C_{18}H_{22}O_7$: 350.1365. Found: 350.1372.
 IR(cm$^{-1}$): 1714, 1478, 1384, 1347, 1136, and 1064.
 $^1$H-NMR ($\delta$, CDCl$_3$): 7.55, 6.85, 4.12, 4.07, 3.97, 3.93, 3.21, 1.54, and 1.33.
 Anal. Calcd. for $C_{18}H_{22}O_7$: C, 61.70; H, 6.33. Found: C, 61.49; H, 6.28.

EXAMPLE 5

Khellin (Formula A-11) Synthesis of Khellin

To a solution of the benzofuran of Formula A-7 (155 mg, 0.442 mmole) in 10 ml of acetonitrile (cooled with an ice bath) is added a solution of cerric ammonium nitrate (728 mg, 1.33 mmole) in 5 ml of water under argon over a period of 10 minutes, and the resulting yellowish orange solution is stirred at 0° C. for an additional 2 hours under argon. The solution is diluted with 20 ml of water and the aqueous layer is extracted three times with 100 ml of chloroform. The combined extracts are washed three times with 50 ml of water, dried over anhydrous sodium sulfate, filtered and concentrated to dryness. The yellowish brown residue is not isolated but is presumably Formula A-8 by NMR, wherein $R_5$ is —$C(OR_{20})(OR_{21})R_6$, $R_{20}$ and $R_{21}$ taken together form a cyclic group of 5 atoms, and $R_6$ is methyl. It is dissolved in 15 ml of THF and treated with 7 ml of an aqueous solution of 1N hydrochloric acid. The resulting solution is stirred at 23° C. for 30 hours, and diluted with 10 ml of water. The aqueous layer is extracted three times with 100 ml of chloroform, and the combined extracts are washed with water, dried over anhydrous sodium sulfate, filtered and concentrated to dryness.

This material is treated with a mixture of ether (5 ml) and n-hexane (10 ml), and the solvents are removed by decantation, yielding an orange brown solid of Formula A-9 (96 mg, 94.4% from the Formula A-7 compound).

The physical properties of this material are the same as those of the authentic sample: $^1$H-NMR ($\delta$, CDCl$_3$): 7.83, 6.98, 6.42, and 2.44. For further purification, the treatment of the orange brown solid of Formula A-9 with a mixture of ether (5 ml), absolute ethanol (5 ml) and n-hexane (10 ml) is repeated, giving 71 mg (70.1%): Mass spectra (m/e): 230, 174, 162, 122, 94, 68, and 66.

The trione of Formula A-9 is treated with 330 mg of sodium bisulfate in 5 ml of water and 1 ml of ethanol. Concentrated hydrochloric acid (0.4 ml) is added to this solution, which is then heated on a steam bath for 1 hour. The resulting solution is cooled and extracted three times with 80 ml of chloroform. The extracts are combined, dried over anhydrous sodium sulfate, filtered and concentrated to dryness. The brown residue is dissolved in 25 ml of dry acetone and heated at reflux with 7 ml of methyl iodide and 200 mg of potassium carbonate for 10 hours. After being cooled, the solvent is removed, and the residue is dissolved in 50 ml of water. The aqueous layer is extracted three times with 80 ml of chloroform and the extracts are combined, washed three times with 100 ml of water, dried over anhydrous sodium sulfate, filtered and concentrated.

TLC analysis shows two spots, which are separated by silica gel thick layer chromatography (developed by 2% methanol in ether three times), yielding 6.4 mg of isokhellin of Formula A-10 and 38.6 mg of the title product (7% and 35% from the Formula A-7 compound, respectively, and 9.7% and 49.6% from the formula A-9 compound, respectively).

Physical characteristics of both synthetic materials are the same as those of the authentic samples.

EXAMPLE 6

4-Acetoxy-5-(1'-dimethyl-t-butylsiloxy)ethyl-6-ethoxy, 7-methoxybenzofuran (Formula A-4: $R_1$ is acetyl; $R_7$ is hydrogen). Reaction of pentacarbonyl[$\alpha$-furyl(methoxy)carbene]chromium (Formula A-1) with 1-ethoxy-3-dimethyl-t-butylsilyloxy-butyne (Formula A-2) in the presence of acetic anhydride (Formula A-3) and triethylamine.

A mixture of the Formula A-1 carbene complex (1.5 g, 5 mmole), the Formula A-2 acetylene (1.5 ml, 7.5 mmole), the Formula A-3 acetic anhydride (0.5 ml, 5 mmole), and triethylamine (0.7 ml, 5 mmole) in tetrahydrofuran (150 ml), prepared under argon, is heated at 65° C. The reaction is monitored by TLC analysis. After 6 hours of heating, an additional 1.5 ml (7.5 mmole) of the acetylene is added to the reaction mixture, which is then heated at 65° C. for an additional 10 hours. After the solvent is removed, the residue is chromatographed by a flash column (silica gel). Elution by 20% ether in n-hexane isolates 893 mg (42.9%) of the title product as a brown oil.

Physical characteristics are as follows:

Mass spectra (m/e): 408, 351, 307, and 280.
Mass Calcd. for $C_{21}H_{32}O_6Si$: 408.1968. Found: 408.1977.
IR(cm$^{-1}$): 1770, 1627, 1480, and 1204.
$^1$H-NMR($\delta$, CDCl$_3$): 7.51, 6.53, 5.36, 4.15–3.95, 4.11, 2.33, 1.56, 1.41, 0.87, and 0.04–0.03.
Anal. Calcd. for $C_{21}H_{32}O_6Si$: C, 61.73; H, 7.90. Found: C, 61.51; H, 8.04.

EXAMPLE 7

5-[1'-(t)-Butyldimethylsilyloxy]ethyl-4,7-dimethoxy-6-ethoxybenzofuran (Formula A-5: $R_{31}$ is methyl; $R_7$ is hydrogen). Preparation of 5'[1'-(t)-butyldimethylsilyloxy-4,7-dimethoxy-6-ethoxy benzofuran.

To a cooled (0° C. by ice-bath) suspension of sodium hydride (50% oil dispersion) (690 mg, 14.4 mmole) in THF (50 ml), prepared under argon, is added a solution of the benzofuran acetate of Formula A-4, (1.95 g, 4.8 mmole) in 50 ml of THF via syringe. The resulting solution is stirred at 0° C. under argon for 1 hour. Methyl iodide (5 ml, a large excess) is introduced to the reaction mixture, and the ice bath is removed. The solution is stirred at 23° C. under argon for 2 days until TLC analysis shows the starting compound is consumed. The resulting solution is poured nto 200 ml of a mixture of ice and water, and the aqueous layer is extracted three times with 100 ml of ether. The extracts are combined, washed three times with 150 ml of brine, dried over anhydrous sodium sulfate, filtered and concentrated. The thick layer chromatography, developed twice by ether:n-hexane (1:9 mixture), isolates the following products: 132 mg (5.7%) of 4-(t)-butyl-dimethylsilyloxy-5-[1'-(t)-butyldimethylsilyloxy]-ethyl-6-ethoxy-7-methoxybenzofuran as colorless needles, 985 mg (54.1%) of the title product as a yellow oil, and 201 mg (19.2%) of 4,7-dimethoxy-6-ethoxy-5-ethenylbenzofuran as a yellow oil.

Physical properties of the products are as follows:
4-(t)-Butyldimethylsilyloxy-5-[1'-(t)-butyldimethylsilyloxy]ethyl-6-ethoxy-7-methoxybenzofuran:
Melting point: 78.5°–80.0° C.
Mass spectra (m/e): 480, 394, 348, and 291.
Mass calcd. for $C_{25}H_{44}O_5Si$: 480.2727. Found: 480.2757.
IR(cm$^{-1}$): 1473, 1347, 1135, and 1053.
$^1$H-NMR ($\delta$, CDCl$_3$): 7.44, 6.72, 5,40, 4.20, 4.06, 1.66, 1.43, 1.09, 0.84, 0.17, 0.12, 0.08, and −0.09.
Anal. Calcd. for $C_{25}H_{44}O_5Si$: C, 62.45; H, 9.22. Found: C, 62.37; H, 9.23.
5-[1'-(t)-butyldimethylsilyloxy]ethyl-4,7-dimethoxy-6-ethoxybenzofuran:
Mass spectra (m/e): 380, 323, 308, 294, 279, and 264.
IR(cM$^{-1}$): 1480, 1378, 1345, 1247, 1132, and 1060.
$^1$H-NMR ($\delta$, CDCl$_3$): 7.51, 6.81, 5.46, 4.16, 4.07, 3.94, 1.62, 1.42, 0,87, 0.09, and −0.04.
Anal Calcd. for $C_{20}H_{32}O_5Si$: C, 63.12; H, 8.48. Found: C, 63.44; H, 8.63.
4,7-Dimethoxy-6-ethoxy-5-ethenylbenzofuran:
Mass spectra (m/e): 248, 233, 219, 188 and 173.
Mass Calcd. for $C_{14}H_{16}O_4$: 248.1048. Found: 248.1033.
IR(cm$^{-1}$): 1607, 1474, 1383, 1338, 1247, 1132, and 1067.
$^1$H-NMR ($\delta$, CDCl$_3$): 7.52, 6.84, 7.09–6.72, 6.19, 5.96, 5.51, 5.37, 4.07, 3.91, 4.05, and 1.39.

EXAMPLE 8

4,7-Dimethoxy-5-(1-hydroxy)ethyl-6-ethoxybenzofuran (Formula A-6: $R_{31}$ is methyl; $R_7$ is hydrogen). Preparation of 4,7-dimethoxy-5-(1'-hydroxy)ethyl-6-ethoxybenzofuran.

Dimethylformamide is added to a mixture of the silyloxybenzofuran of Formula A-5 (600 mg, 1.58 mmole) and tetra-n-butyl-ammonium fluoridetrihydrate (1.5 g, 4.74 mmole), prepared under argon, at 23° C. The resulting solution is stirred at 23° C. under argon for 20 hours, and diluted with 250 ml of ether. The ether extract is washed five times with 150 ml of brine, dried over anhydrous sodium sulfate, filtered, and concentrated. The product is purified by thick layer chromatography (silica gel, developed by ether:n-hexane (1:1 mixture)), giving 355 mg (84.5%) of the title product as a yellow oil.

Physical characteristics are as follows:

Mass spectra (m/e): 266, 251, and 222.

Mass Calcd. for $C_{14}H_{18}O_5$: 266.1154. Found: 266.1151.

IR(cm$^{-1}$): 3467, 1613, 1480, 1385, 1343, 1245, 1132 and 1059.

$^1$H-NMR ($\delta$, CDCl$_3$): 7.52, 6.83, 5.40–5.10, 4.21, 4.05, 3.73, 1.56, and 1.44.

Anal. Calcd. for $C_{14}H_{18}O_5$: C, 63.14; H, 6.81. Found: C, 63.19; H, 6.80.

EXAMPLE 9

5-Acetyl-4,7-dimethoxy-6-ethoxybenzofuran (Formula B-1: $R_{31}$ is methyl). Preparation of 5-acetyl-4,7-dimethoxy-6-ethoxybenzofuran.

The corresponding alcohol of Formula A-6 (1.35 g, 5.1 mmole) and pyridinium dichromate (4.0 g, 10.2 mmole) are placed in a 500 ml round-bottomed flask, which is evacuated and filled with argon. Dry methylene chloride (200 ml) is added to the mixture at 23° C. The resulting dark solution is stirred at 23° C. under argon for 36 hours. The reaction solution is diluted with 300 ml of methylene chloride and filtered through the celite and silica gel layers. The filtrate is concentrated by rotary evaporation and loaded on silica gel thick layer plates (developed by ether:n-hexane (3:5 mixture)), giving 711 mg (53.1%) of the title product as a yellow oil.

Physical characteristics are as follows:

Mass spectrua (m/e): 264, 221, and 175.

Mass Calcd. for $C_{14}H_{16}O_5$: 264.0998. Found: 264.1006.

IR(cm$^{-1}$): 1707, 1611, 1479, 1384, 1352, 1137, and 1070.

$^1$H-NMR ($\delta$, CDCl$_3$): 7.55, 6.86, 4.23, 4.07, 3.98, 2.53 and 1.33.

Anal. Calcd. for $C_{14}H_{16}O_5$: C, 63.62; H, 6.10. Found: C, 63.72; H, 6.19.

EXAMPLE 10

5-Acetoxy-4,7-dimethoxy-6-hydroxybenzofuran (Formula B-2: $R_{31}$ is methyl). Preparation of Khellinone.

To a cooled solution (by ice bath) of the benzofuran of Formula B-1 (103 mg, 0.39 mmole) in 70 ml of dry methylene chloride is slowly added boron trifluoride etherate (0.5 ml) under an argon atmosphere. During this procedure, the solution turns yellow. The ice-bath is removed and the reaction solution is warmed up to 23° C. at which point the color turns to wine red. The resulting solution is stirred at 23° C. under argon for 15 hours, and diluted with 50 ml of methylene chloride. The methylene chloride extract is washed three times with 100 ml of water, dried over anhydrous sodium sulfate, filtered and concentrated. The product (single spot on TLC) is purified by thick layer chromatography (silica gel, developed by 25% ether in n-hexane), giving 89 mg (96.7%) of the title product as a yellow crystalline.

Physical properties of the product are the same as the authentic sample:

Mass spectra (m/e): 236, 221, 206 and 203.

Mass Calcd. for $C_{12}H_{12}O_5$: 236.0685. Found: 236.0679.

IR(cm$^{-1}$): 3160, 1694, and 1679.

$^1$H-NMR ($\delta$, CDCl$_3$): 13.12, 7.50, 6.89, 4.13, 4.03, and 2.71.

EXAMPLE 11

Khellin (Formula B-3) Synthesis of khellin

To a mixture of khellinone of Formula B-2 (80 mg, 0.339 mmole) and sodium hydride (50% oil dispersion) (163 mg, 3.39 mmole), prepared under argon, is added 15 ml of ethyl acetate via syringe. The yellow mixture is heated at reflux for 6 hours under argon. After being cooled, the solution is poured into a mixture of ice-water and acidified (pH of approximately 1) by concentrated hydrochloric acid. The aqueous layer is extracted three times with 50 ml of methylene chloride. The combined extracts are washed with water, dried over magnesium sulfate, filtered and concentrated to dryness. The yellow residue is dissolved in methanol (30 ml) and 1N hydrochloric acid (15 ml), and stirred at 23° C. for 48 hours. The solvent is removed by rotary evaporation and the residue is dissolved in 50 ml of water. The aqueous layer is extracted three times with 50 ml of methylene chloride and the extracts are combined, washed three times with 50 ml of water, dried over anhydrous sodium sulfate, filtered and concentrated. The product is purified by silica gel thick layer chromatography (eluted by ether), giving 73 mg (83% overall) of the title product as colorless needles.

Physical properties of the synthetic material are the same as those of the authentic sample.

EXAMPLE 12

5-Ethoxycarbonyl, 4-hydroxy, 7-methoxy benzofuran (Formula C-3: $R_{11}$ is ethyl). Reaction of pentacarbonyl[2'-furyl(methoxy)carbene]chromium (Formula C-1) with ethyl propiolate (Formula C-2).

A mixture of the Formula C-1 carbene complex (2.5 g, 8.27 mmole) and ethyl propiolate of Formula C-2 (1.26 ml, 12.4 mmole) in tetrahydrofuran is heated at 60° C. under an argon atmosphere for 6 hours. TLC analysis shows the starting carbene is not consumed. Another 12.4 mmoles (1.26 ml) of acetylene is added and the mixture is heated for an additional 7 hours, at which point the reaction is complete. After cooling, the solvent is removed and the black residue is chromatographed through a column of silica gel using a flash chromatography. Elution by 5%–10% ether in n-hexane gives 349 g (20.5%) of the title product as colorless crystals; elution by 10% ether in n-hexane affords trace (less than 5%) of [2'-($\alpha$-furyl),2'-methoxy]ethenyl propionic acid ethyl ester, as a colorless oil, and 453 mg (19.4%) of [2'-($\alpha$-furyl), 2'-methoxy]ethenyl malonic acid diethyl ester as a colorless oil.

The physical properties of the products are as follows: 5-Ethoxycarbonyl, 4-hydroxy, 7-methoxy benzofuran:

Mass spectra (m/e): 236, 190, 162, and 147.
IR(cm$^{-1}$): 1664, 1616, 1535, 1483, 1475, and 1377.
1H-NMR (δ, CDCl$_3$): 11.23, 7.59, 7.18, 6.98, 4.44, 3.97, and 1.43.
Anal. Calcd. for $C_{12}H_{12}O_5$: C, 61.01; H, 5.12. Found: C, 61.13; H, 5.14.

Diethyl[2'-(α-furyl),2'-methoxy]ethenyl malonate (E isomer):

The physical properties are the same as those of authentic material. Ethyl]2'-(α-furyl),2'-methoxy]ethenyl propionate (as a mixture of two isomers):

NMR (δ, CDCl$_3$): 7.40–7.25, 6.50–6.30, 4.88, 4.08, 3.70 and 3.68, 3.40 and 3.25, and 1.25.

EXAMPLE 13

5-Acetyl, 4-hydroxy, 7-methoxy benzofuran (Formula C-4). Reaction of Pentacarbonyl[2-furyl(methoxy)carbene]chromium (Formula C-1) with 3-butyn-2-one (Formula C-2(a)).

A THF solution (100 ml) of the Formula C-1 carbene complex (302 mg, 1 mmole) and Formula C-2(a) acetylene (0.2 ml, 2.6 mmole), prepared under an argon atmosphere, is heated at 60° C. for 3 hours. After being cooled, the solvent is removed and the black residue is loaded on a silica gel plate (2000 micron), which is developed by 20% ether in n-hexane four times giving 18 mg (13%) of the title product as colorless crystals.

Physical characteristics are as follows:
Mass spectra (m/e): 206, 191, 173, 151, and 95.
1H-NMR (δ, CDCl$_3$): 10.12, 7.60, 7.01, 4.00, and 2.64.

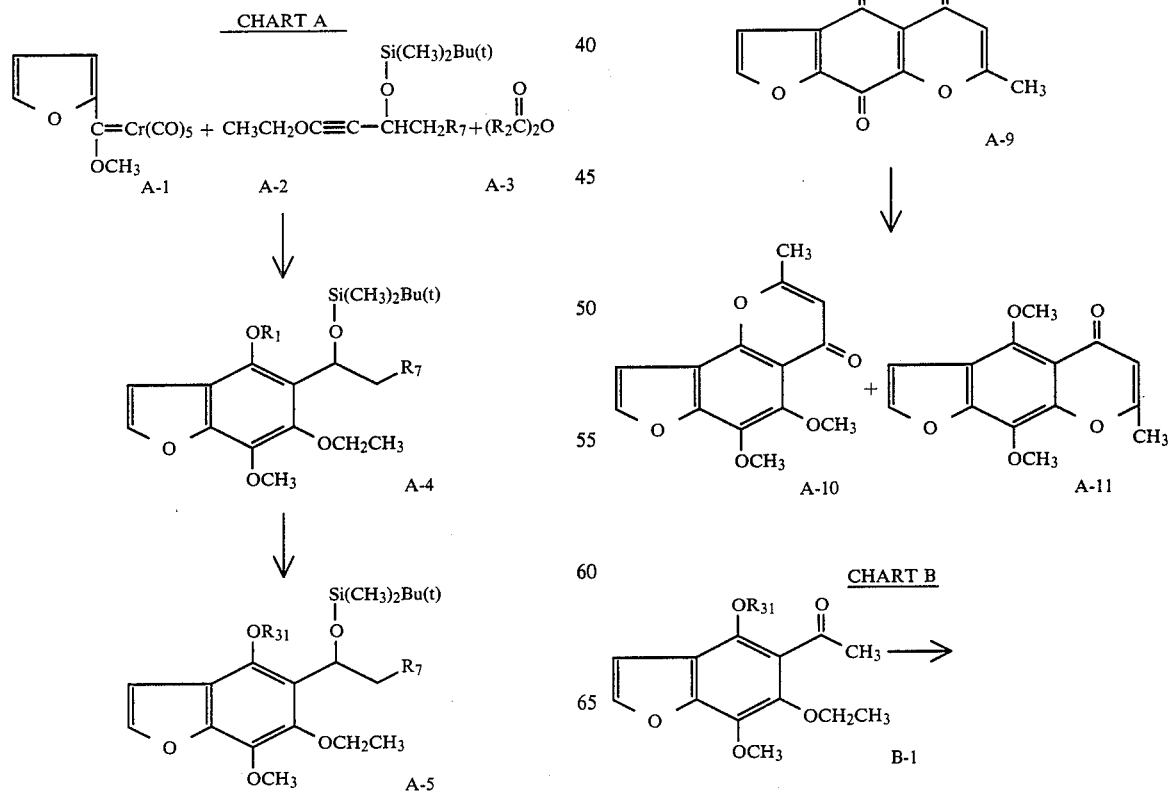

CHART A

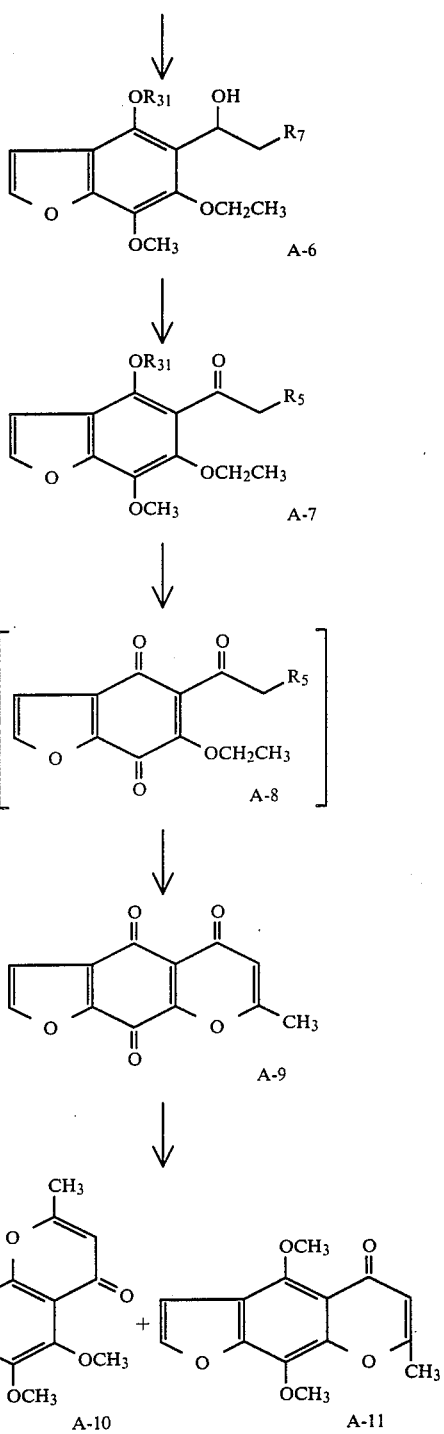

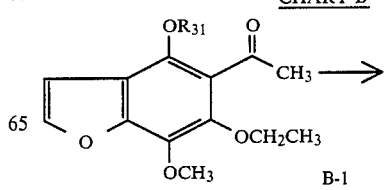

CHART B

-continued
CHART B
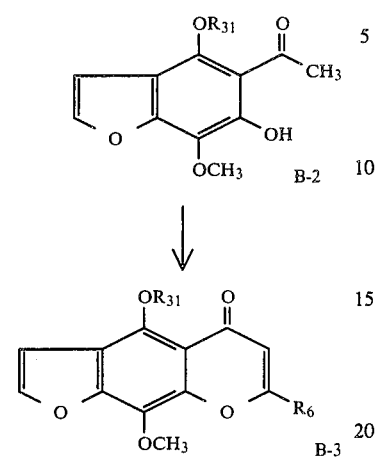
CHART C
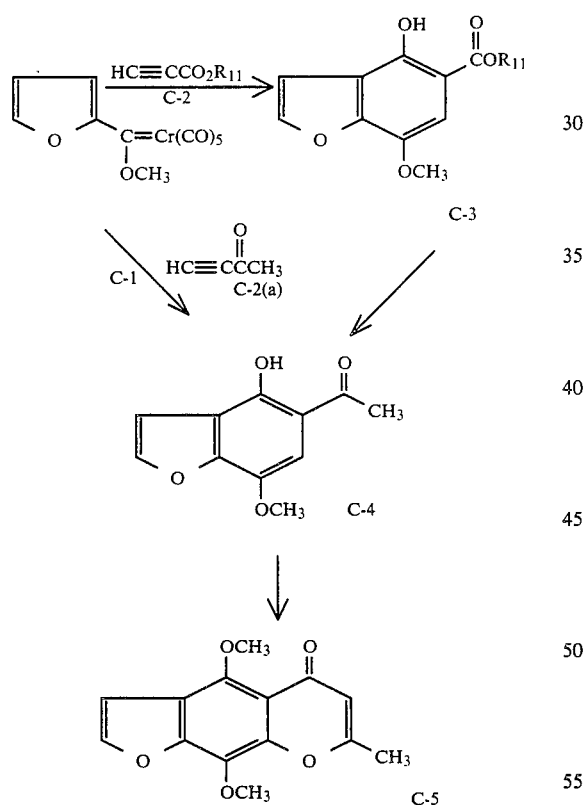
FORMULAS
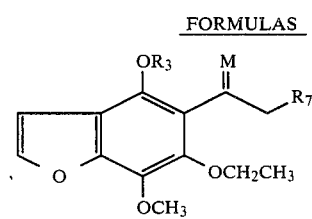
I
-continued
FORMULAS
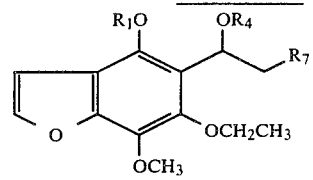
II
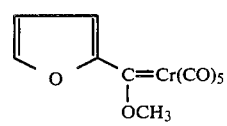
III
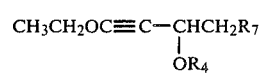
IV
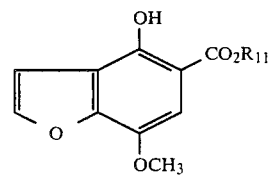
VII
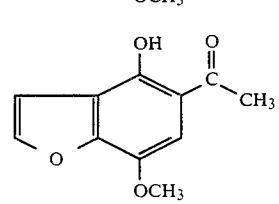
VII(a)
$HC{\equiv}CCO_2R_{11}$  VIII
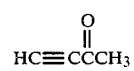
VIII(a)
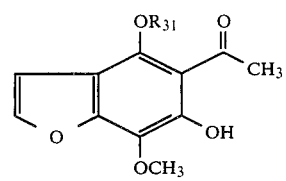
IX
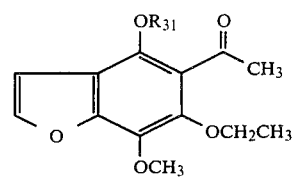
X
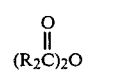
XI
I claim:
1. A process for preparing a compound of the formula II
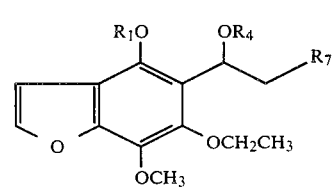
II wherein R₁ is —C(O)—R₂;
wherein R₂ is (C₁-C₅) n-alkyl;
wherein R₄ is
 (a) —SiR₁₂R₁₃R₁₄,
 (b) benzyl, or
 (c) benzyl substituted by 1 to 3 (C₁-C₄)alkyl or 1 or 3 (C₁-C₄)methoxy groups;
wherein R₇ is
 (a) hydrogen,
 (b) —C(O)—R₆, or
 (c) —C(OR₂₀)(OR₂₁)R₆;
wherein R₆ is
 (a) (C₁-C₈)alkyl,
 (b) (C₂-C₈)alkoxymethyl,
 (c) trifluoromethyl,
 (d) phenoxymethyl,
 (e) phenylthiomethyl, or
 (f) —CH₂—S(O)ₙ—R₂₂;
wherein n is 0, 1, or 2;
wherein R₁₂, R₁₃, and R₁₄ are the same or different and are:
 (a) (C₁-C₄)alkyl, or
 (b) phenyl;
wherein R₂₀ and R₂₁ are the same or different and are
 (a) C₁-C₄)alkyl, or
 (b) R₂₀ and R₂₁ taken together form a cyclic group of from 5 to 6 atoms; and
wherein R₂₂ is (C₁-C₅)alkyl;
which comprises reacting a chromium compound of the formula III

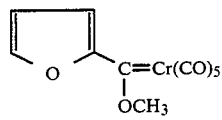

III with an acetylenic compound of the formula IV

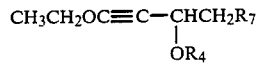

IV in the presence of an acid anhydride of the formula XI

XI and triethylamine to yield the formula II compound.

2. A process of claim 1 wherein R₇ is hydrogen.
3. A process for preparing a compound of the formula IX

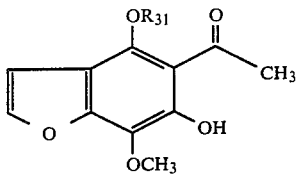

IX wherein R₃₁ is (C₁-C₅)alkyl;
which comprises treating a compound of the formula X

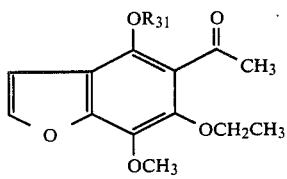

X with a Lewis acid to yield the formula IX compound.

4. A process for preparing a compound of the formula VII(a)

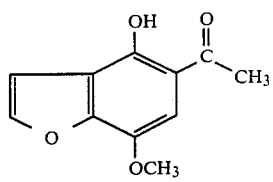

VII(a)

which comprises reacting a chromium compound of the formula III

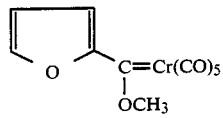

III with an acetylenic compound of the formula VIII(a)

VIII(a)

to yield the formula VII(a) compound.

* * * * *